United States Patent [19]

Lorente et al.

[11] Patent Number: 4,918,739
[45] Date of Patent: Apr. 17, 1990

[54] PROCESS AND SYSTEM FOR DIGITAL ANALYSIS OF IMAGES APPLIED TO STRATIGRAPHIC DATA

[75] Inventors: Maria A. Lorente; Jeanny T. De Rincon; Orlando Morean; Terence B. Wright, all of Caracas, Venezuela

[73] Assignee: Maraven, S.A., Caracas, Venezuela

[21] Appl. No.: 231,724

[22] Filed: Aug. 12, 1988

[51] Int. Cl.[4] .............................................. G06K 9/00
[52] U.S. Cl. ........................................ 382/1; 382/16; 382/18; 358/107
[58] Field of Search ...................... 382/1, 6, 16, 18, 25, 382/28, 48, 51, 57; 358/106, 107; 356/71; 364/413

[56] References Cited

U.S. PATENT DOCUMENTS

| | | | |
|---|---|---|---|
| 3,999,047 | 12/1976 | Green | 382/6 |
| 4,000,399 | 12/1976 | Kawahara | 382/18 |
| 4,229,797 | 10/1980 | Ledley | 358/106 |
| 4,453,266 | 6/1984 | Bacus | 382/6 |
| 4,503,555 | 3/1985 | Brimhall, Jr. et al. | 382/6 |
| 4,513,438 | 4/1985 | Graham et al. | 382/6 |
| 4,554,580 | 11/1985 | Hayashi | 358/107 |
| 4,592,089 | 5/1986 | Hartman | 358/107 |
| 4,598,419 | 7/1986 | Mignot et al. | 382/6 |
| 4,700,298 | 10/1987 | Palcic et al. | 364/414 |
| 4,791,675 | 12/1988 | Deering et al. | 382/18 |

FOREIGN PATENT DOCUMENTS 2029570 3/1980 United Kingdom .

*Primary Examiner*—Leo H. Boudreau
*Assistant Examiner*—Jose L. Couso
*Attorney, Agent, or Firm*—Bachman & LaPointe

[57] ABSTRACT

A system and a process are disclosed for the quantitative characterization of organic matter concentrates and of petrographic thin sections or polished fragments of rocks found in oil reservoir samples. The system includes a video camera for capturing images from a microscope or a series of photographs. An electronic digitizer for digitizing and storing the images, and a microprocessor for performing digital image processing operations. Morphological data such as area, perimeter, width, length, and orientation of particles are obtained from the digital representation of the particles by means of algorithms based on the principles of connectivity and the theory of moments. The process permits the automation of quantitative sedimentological and palynological analyses and the stastistical characterization of the samples based on widely-used geological parameters derived from the morphological data. The system also includes at least one monitor for displaying any of the images being processed and a printer for generating a graphical output of the statistical distributions.

16 Claims, 4 Drawing Sheets

STEP 1 STEP 2

STEP 3 STEP 4

STEP 5 STEP 6

STEP 7 STEP 8

GRANULOMETRY (SUMMATORY OF AREAS)

MZ= 3.07
SO= -1.18
KG= 0.92
SKI= -0.33
DE = 1.79

NUMBER OF PARTICLES IN THE GRAPH = 741
NUMBER OF PARTICLES IN THE SAMPLE = 1009
MAX. NUMBER OF PARTICLES (DRAWING/RATIO) = 48

PROCESS AND SYSTEM FOR DIGITAL ANALYSIS OF IMAGES APPLIED TO STRATIGRAPHIC DATA

CROSS REFERENCE TO RELATED APPLICATIONS

The present application is assigned to the same Assignee as co-pending application Ser. No. 683,839, filed July 1, 1987, to Terence B. Wright for a Process and Apparatus For Determining Flow Rate Of A Flow Medium In A Flow Line, now U.S. Pat. No. 4,837,708.

BACKGROUND OF THE INVENTION

The present invention relates to digital image processing systems and processes for quantitative particle characterization and, more particularly, to a system and a process for automatic characterization of palynological and sedimentological samples based on algorithms implementing techniques of image enhancement, connectivity and morphological analysis, operating on the objects or patterns in an input image obtained by means of a TV camera.

Textural description of organic matter particles by size and shape has previously been performed by direct measurement of each particle using a visual scale through a viewing device, usually a microscope, for quantitative data, and by comparison with visual charts for qualitative data.

Pore size determinations and rock mineral analysis has traditionally been done either by counting unit areas (point counting) with a mechanical device or by manual planimetry of a projected image.

These measurement methods have the disadvantage of being very subjective to operator opinion and are also very time consuming.

Early techniques for the quantitative characterization of organic remains were first mentioned in the literature by M. A. Lorente in a paper entitled PALYNOLOGY AND PALYNOFACIES OF THE UPPER TERTIARY IN VENEZUELA. The paper discussed some basic concepts for transforming the raw data on observed organic matter particles as obtained by a QUANTIMET device into geologically meaningful parameters.

The patent literature is characterized by several patents in the field of particle analysis.

U.S. Pat. No. 4,229,797 describes a method and system for whole picture image processing, in particular for automatic measurement of texture and color by an electronic device, whereby certain parameters are obtained by effective electronic subtraction of an original first image from a "smoothed" (locally averaged) second image to obtain local maxima, which points are further used to calculate first, second and third moments of objects as parameters that could be compared with tables or predetermined standard patterns of texture representing known classifications of medical objects.

UK patent application Ser. No. 2,029,570-A, describes a method and apparatus for image analysis and automatic classification of a field of objects that uses interaction with an operator to select a threshold image intensity value to distinguish a set of objects in the field of view, considered by the operator as belonging to a particular class of objects, from all other such objects. Automatic measurement and storage of the threshold value and other computed parameters describing the selected objects permits the device to later classify objects in other images as belonging to a previously described class. This published patent application specifically refers to a QUANTIMET image analyzer device intended to be used to measure total porosity and to quantify shape, size distribution and connectivity of pores for quantifying grain shape in soils and sediments. This invention has the disadvantage of requiring a device of great complexity and consequent high cost, whose nature is fixed and therefore inflexible. It also relies on the judgement of an operator to calibrate the classification system. Further disadvantages of the noted complexity are the consequent high cost and the relative untransportability to remote operating areas in the geological sciences.

U.S. Pat. No. 4,700,298 describes a microscope image processing scanner for locating, measuring and recognizing live cells growing in tissue culture flasks. The main objective of the invention is to locate, identify and track moving cells in a dynamic environment. The described technique is limited to determining the presence and location of a cell in two dimensions within the field of view. Measurements of image density are used to identify cells from debris and other inconsequential objects. No form or shape parameters are extracted.

Generally, these systems are not suitable for use in the quantitative characterization of organic matter concentrates and of petrographic thin sections or polished fragments of rock found in oil reservoir samples.

Accordingly, it is an object of the present invention to provide a system and process for use in the quantitative characterization of organic matter concentrates and of petrographic thin sections or polished fragments of rock found in oil reservoir samples.

It is a further object of the present invention to provide a system and process as above which obtains morphological data about samples using image digital analysis techniques.

These and other objects and advantages of the present invention will become more apparent from the following description and drawings in which like reference numerals depict like elements.

SUMMARY OF THE INVENTION

The present invention involves a system and a process for image digital analysis to achieve morphological characterization of image components. The system and process use a quantitative analysis of 2-dimensional gray-scale images, with emphasis in the measurement of the morphological properties and statistical distribution of particles present in the images.

The system of the present invention broadly comprises a means for digitizing and storing images captured by a TV camera. The informational content of the digital representation of the images includes an array of 512 by 480 picture elements with a resolution of 128 gray-levels. The system also includes means for displaying the gray-level images on a high resolution monitor.

The system further includes means for improving the digitized image, means for processing the improved digitized image, means for transforming raw two dimensional digitized data into statistical distribution representing the components of the sample, and means for graphically displaying an output comprising the statistical distributions. The output preferably includes statistical curves and parameters which can be used to characterize the sample images. The image improving means preferably comprises means for editing the images to eliminate undesired portions. In a preferred embodiment the processing of the improved digitized image and the transformation of the raw data is performed by a general purpose microprocessor which has been preprogrammed to perform a desired set of operations and which has an interface with an operator-instructor.

The process of the present invention includes performing gray-level transformations of the digitized images in order to emphasize desired properties of the objects present in the images. Location of an area of interest where processing will take place is user-selectable. A binary quantization using thresholding techniques takes place before spatial operations are performed on the data. A contour tracking algorithm based on an 8-connectivity concept is applied to the objects in the area of interest of the image and ij-th moments are computed for every object. Based on this information, morphological measurements such as eccentricity, area, perimeter, and orientation, are determined.

A better understanding of the principles and details of the present invention will be evident from the following description and drawings.

DETAILED DESCRIPTION OF THE PREFERRED EMBODIMENT

The detailed operation of the integrated system will be described hereinbelow with reference to the Figures.

The present invention involves a system and a process for the quantitative analysis of 2-dimensional grayscale images and, more particularly, the measurements of the morphological properties and statistical distributions of particles present in the images by defining attributes of the images as a function of predetermined gray codes.

Figure 1:
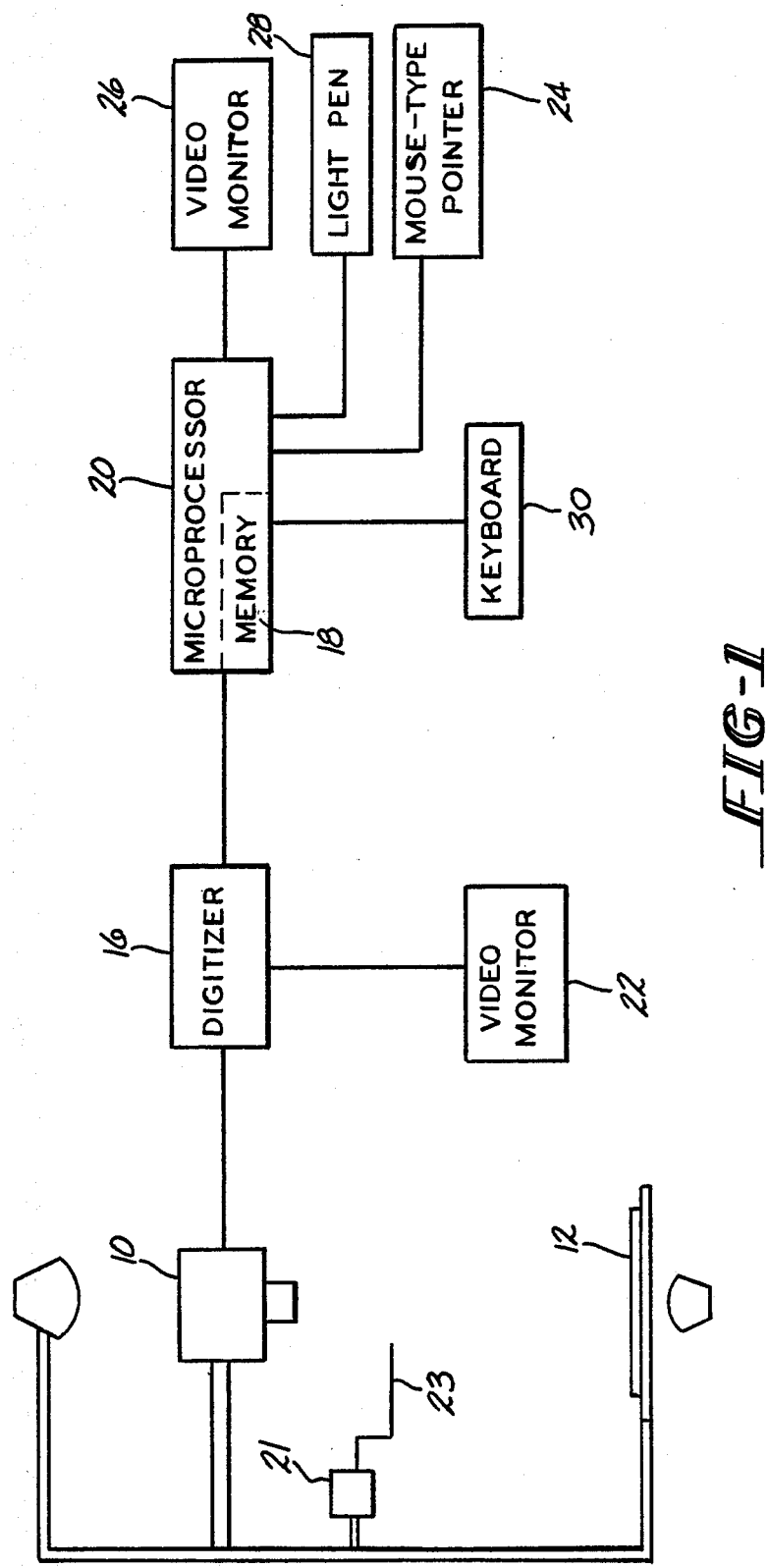
FIGS. 1 and 2 are schematic illustrations of the system of the present invention.
Figure 2:
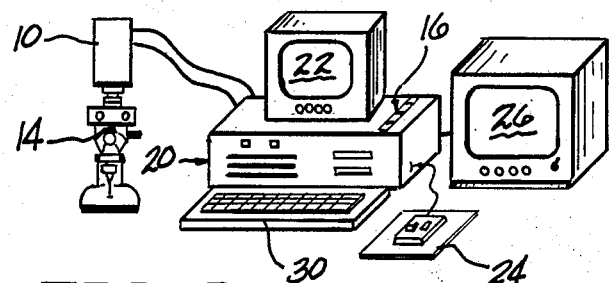

In general, the process and integrated system of the present invention as shown in FIGS. 1 and 2, comprises capturing a series of images by means of a TV camera 10. The images may be a series of photographs 12 of samples to be measured or images from the lens of a microscope 14. The camera 10 is preferably a monochromatic video camera such as an RS-170 video camera because such a camera has a higher spatial resolution than a color video camera. Using such a camera, it is possible to generate a digital representation of the images whose informational content includes an array of 512×480 picture elements with a resolution of 128 gray levels.

The camera 10 may be fitted with an adjustable lens system and an aperture diaphragm, both not shown, to correctly focus and adjust the quantity of received light. Suitable adjustable lens systems and aperture diaphragms for achieving these goals are known in the art and do not form part of the present invention.

An electronic digitizer 16 receives the video signals of the image(s) captured by the camera 10 and translates the images into machine readable format. The digitizer 16 may comprise any suitable device known in the art having appropriate circuitry for converting each image into a digital matrix representing two dimensions in cartesian coordinates and containing values representing measurements by the camera of relative light intensities over its field of view. The digitized images(s) may be transferred to the memory 18 of a microprocessor 20. A first high resolution video display monitor 22 such as a CRT linked to the digitizer 16 may be used to display the image(s) being received from the camera 10 or stored in the memory of the digitizer and/or the memory of the microprocessor 20.

The microprocessor 20 may comprise any suitable computer known in the art and may be provided with appropriate modules or cards and/or suitable programming for performing a variety of functions and operations. For example, the microprocessor may be a desktop computer such as an IBM-PC/AT having a 512 KB RAM, a 20MB hard disk, an associated color monitor 26, and a digitization and a frame grabber card 16. The microprocessor 20 may have a mouse interface 24 and/or a light pen interface 28 to ease the task of image editing. The microprocessor 20 is used to generate a number of derived images, each of which contains a representation of the captured image through interpretation of the shades and/or light intensities and through the use of mathematical and/or logical operations such as transformations, comparisons, additions, subtractions, correlations, and/or multiplications.

Prior to using the system to perform quantitative analysis of the images(s), it is necessary to calibrate the system in order to determine the correspondence between measurements in pixels (i.e. picture elements) and the actual real-life values. In a preferred approach, calibration is accomplished by measuring the length of a high-precision reference, both horizontally and vertically. Measurement may then be performed by changing the dimensions of the area of interest until it exactly covers the reference. In a preferred approach, calibration is performed for every magnification of the microscope 14.

The microprocessor 20 may be provided with suitable programming for performing the above mentioned calibration techniques. Once calibrated, there exists an accurately known linear relationship between the real separation of two points in each of two normal cartesian coordinate axes on a real subject image, and a calculated separation of images of the same two points in the digitized image. Information received by the microprocessor 20 from the calibration process may be stored and used to normalize the quantitative analysis of a set of related images and system setup. The calibration process also facilitates computations and permits the use of different camera lens systems as well as adjustments for anticipated changes over time in the location of the camera and the size and shape of its viewing area.

After completion of the initial setup and calibration steps, a subject sample may be examined. For example, a subject sample may be placed under the microscope 14. The microscope and/or camera are then focused until a clearly defined image is observed in the high resolution monitor 22. Repetitive analog images of the sample are produced by viewing the sample substantially continuously with the camera. The repetition frequency of a video camera is typically thirty times per second.

After the image captured by the camera 10 has been digitized by the digitizer 16 and stored in the microprocessor memory 18 and/or displayed on the video monitor 22, the operator selects one of several available processing strategies in order to perform a quantitative analysis of the particles distinguished in the image. The available strategies include: (1) controlling the level of intensity and contrast of the gray-scale image; (2) selecting the level of threshold; (3) image filtering; (4) editing the threshold image; and (5) processing for quantitative analysis. The following flow chart illustrates a menu driven program interface for performing the various steps in the above strategies.

---

ADIE Main Menu

I. Environment menu
   A. System initialization
   B. System calibration
   C. Work area II. Task Menu
   A. New Task
   B. Read file
   C. Menu of Palynology
      1. Menu of Image Editing
         Output Threshold
         Gray scale Adjust
         Erase Particles
         Separate Particles
         New Image acquisition
      2. Menu of Image Processing
         Menu of Image Editing
         Output Threshold
         Gray scale Adjust
         Erase Particles
         Separate Particles
         New Image acquisition
         Processing Images
         Read file
         Save file
         New task
         Menu of grafication
         Granulometric Distribution
         Histograms of areas
         Relative elongation
         Relative Irregularity
      3. Palynology Counter Menu
         Maceral Selection
         Menu of Image Editing
         Output Threshold
         Gray scale Adjust
         Erase Particles
         Separate Particles
         New Image acquisition
         Process the Image
         Read file
         Save file
         New Task
      4. Menu of grafication
         Granulometric Distribution
         Histograms of areas
         Relative elongation
         Relative Irregularity
   D. Menu of Sedimentology
      1. Menu of Image Editing
         Output Threshold
         Gray scale Adjust
         Erase Particles
         Separate Particles
         New Image acquisition
      2. Characterization Menu
         Menu for processing pores
         Processes the Images
         Menu of Image Editing
         Output Threshold
         Gray scale Adjust
         Erase Particles
         Separate Particles
         New Image acquisition
         Read file
         Save file
         New task
         Menu of grafication
         Granulometric Distribution
         Histograms of areas
         Relative elongation
         Relative irregularity
         Orientation
         Menu for Particles processing
         Menu of Image Editing
         Output Threshold
         Gray scale Adjust
         Erase Particles
         Separate Particles
         New Image acquisition
         Read file
         Save file
         New Task
         Menu of grafication
         Granulometric Distribution
         Histograms of areas
         Relative elongation
         Relative irregularity
         Orientation
      3. Menu for Sedimentology Counter
         Menu for Minerals counter
         Minerals Selection
         Menu of Image Editing
         Output Threshold
         Gray scale Adjust
         Erase Particles
         Separate Particles
         New Image acquisition
         Image processing
         Read file
         Save file
         New Task
         Minerals Classification

---

Depending upon the strategy selected by the operator, the microprocessor 20 executes the series of mathematical and/or logical operations needed to perform the selected strategy, for example, capturing one image, selecting the point-to-point transformation at the input of the digitizer, selecting the central gray-level and span of a band-pass or band-reject filtering of the gray-level image, or in the case of editing operations, allowing the operator to perform the desired operations with a manually-operated device and visualizing the results directly on the monitor 22 or 26. The manually-operated device may comprise a conventional mouse-type pointer 24 and/or a light pen 28. It is also possible to program the system for performing the available strategies in manual mode. In this mode, a keyboard 30 is used to issue instructions to perform the selected operations.

Controlling the level of intensity and contrast of an image can be achieved by modifying the point-to-point transformation taking place at the input of the digitizer 16. By selecting a negative slope linear transformation, for example an inverted image can be obtained. This is particularly useful in the quantitative study of voids and the determination of porosity in the sample images based on the same algorithms. One of the advantages of the present invention is that the results of these operations can be continuously monitored by the operator.

In order to facilitate characterization and/or identification of the objects in the images, certain threshold levels may be established. The selection of a threshold level may be done manually by the operator and is desirable because it permits one to determine the optimum binary representation of a digitized sample image with minimum influence of noise possible and maximum definition of target objects. The quantitative analysis can then be performed on the thresholded image. If desired, selected threshold values may be updated by the operator. Further, the range of input and output gray levels of an image can be modified by means of hardware supplemented input and output look-up tables.

Image editing permits elimination of undesired traces, spots, objects in the area of interest not to be included in quantitative analysis, or the like, from the digitized image. Editing has block and line modes to perform coarse and detailed operations respectively. Editing also permits the addition of features to the image as well as erasure. For example, missing components can be added to the image. As previously discussed image editing may be performed using the mouse-type pointer 24 and/or the light pen 28.

In certain cases, it might be convenient to perform global modifications to the image by means of a filter 23 and conventional filter actuation means 21. The filtering operation(s) may be used to select only objects whose gray-levels are in a specified gray-level range. For example, the operator can select the gray-level at the center of a desired range by means of the mouse-pointing device 24. Through the use of control keys on the microprocessor 20, the operator can activate/deactivate the selected filtering operation, change the parameters of the filter, and select band-pass or band-reject modes.

After all modifications to the sample image have been performed, the operator proceeds to apply the processing routines aimed at obtaining the morphological parameters which will serve as the basis for the quantitative analysis and statistical characterization of the sample image. Processing is preferably carried out inside an area of interest on the image. During processing, the area of interest is scrutinized on a line-by-line fashion to locate clusters of pixels with a gray-level below a threshold level selected by the operator. These clusters correspond to objects whose morphological properties are going to be determined by the digital processing algorithms. These objects can be referred to as "target objects".

Once a target object is located, its border pixels can be tracked by a contour following algorithm known as the Turtle algorithm based on the 8-connectivity concept in which in a two dimensional rectangular pixel matrix, two pixels are eight connected if they are connected by a face or a corner.

Figure 3:
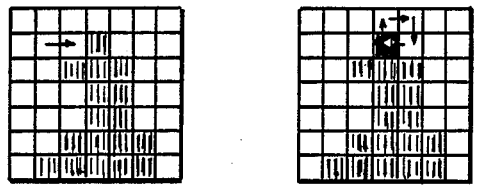
FIG. 3 illustrates the processing steps of a contour following algorithm known as the Turtle algorithm.
Figure 3:
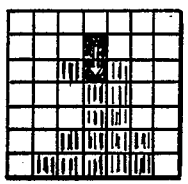
Figure 3:
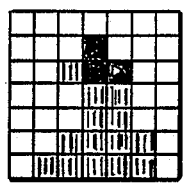
Figure 3:
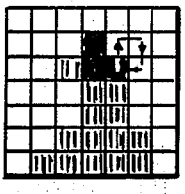
Figure 3:
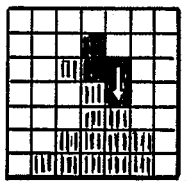
Figure 3:
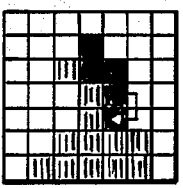
Figure 3:
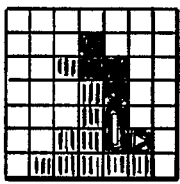
Figure 4:
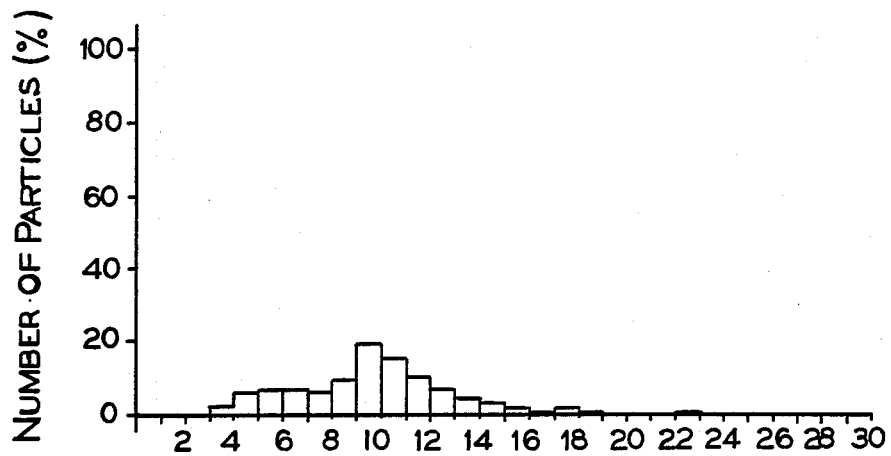
FIG. 4–7 illustrate a portion of the output generated by the system and the process of the present invention.
Figure 5:
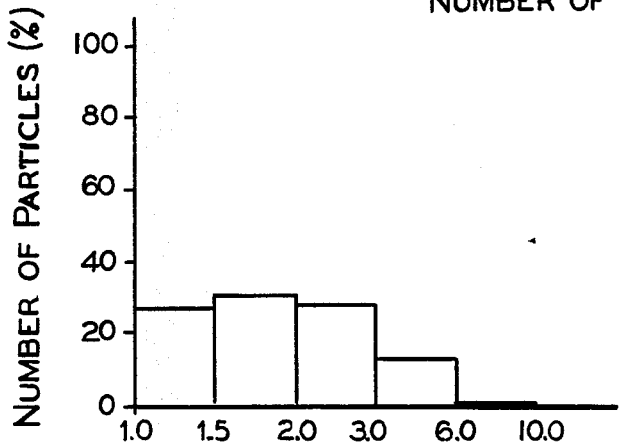
Figure 6:
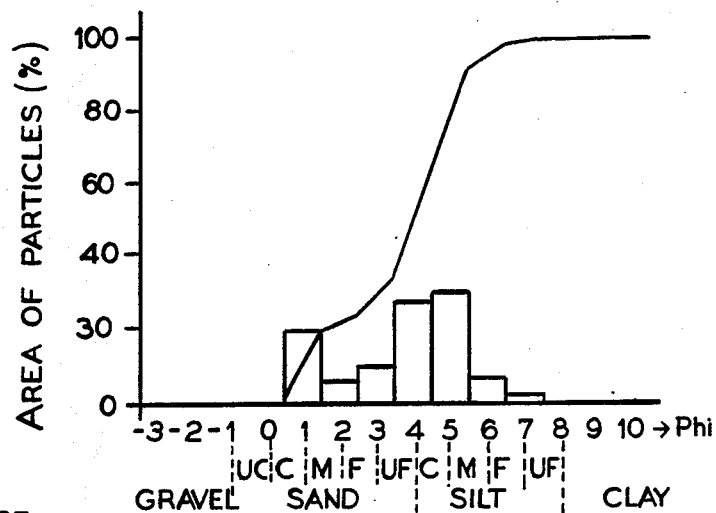

FIG. 3 illustrates the processing steps of this algorithm. In step 1, the target object is entered horizontally. As shown in Table I, this is classified as a Type 2 facet crossing. In step 2, the target object is left or exited vertically in a way which is classified as a Type 5 crossing. This is followed by a horizontal entry of the target object (Type 4). Internal and external facets of the target object are traversed from step 1 to step 8 as the contour following algorithm tracks the border of the target object.

The borders of the target objects are "marked" using a preselected binary system code not contained in a range of gray-level codes generated by the image digitizer. Marking the border pixels permits the searching algorithm to skip already processed target objects. The contour following algorithm is designed to skip over "weak" connections of target objects. Two target objects can be said to be weakly connected if the objects are 8-connected by just one pixel in the diagonal direction. In a more general context, an operation of erosion, a process by means of which the perimeter of a particle present in the image is gradually reduced, may be performed to break strong connections (i.e. 8-connection trough 1 or more pixels).

Every pixel in an image is preferably identified by cartesian coordinates relative to a reference point, generally located at one of the corners or at the center of the digitized image plane. In a preferred embodiment, the digitized image is represented as a 2-dimensional array of rectangular pixels and, therefore, every pixel has 4 facets, i.e. 2 horizontal and 2 vertical facets. Every target object is a cluster of inner and border pixels. Border pixels are characterized by having internal and external facets. An internal facet corresponds to a common facet joining two pixels that belong to the same object. An external facet corresponds to the interface between a border pixel of a target object and its surroundings. Internal and external facets are traversed as the contour following algorithm tracks the border of the target object. Only external facet crossings contribute to the calculation of the moments of the target objects which can be done using a cumulative process.

As discussed before, external facet crossings can be characterized by the direction and sense of movement while the crossing takes place. Additionally, an external facet crossing implies leaving the target object into the surroundings, or entering the target object from its surroundings. Consequently, eight types of external facet crossings can be identified, as shown in Table 1.

TABLE 1
EXTERNAL FACET CROSSINGS TYPES

| Type | Direction | Sense | Relation to the Target Object |
|---|---|---|---|
| 1 | horizontal | right | leaving |
| 2 | horizontal | right | entering |
| 3 | horizontal | left | leaving |
| 4 | horizontal | left | entering |
| 5 | vertical | up | leaving |
| 6 | vertical | up | entering |
| 7 | vertical | down | leaving |
| 8 | vertical | down | entering |

The contour following algorithm generates the coordinates of the pixels defining the border of the target object. Based on this information and the knowledge of the type of external facet crossing, the following quantities can be calculated through a cumulative process:
SUMX: sum of the x-coordinates
SUMY: sum of the y-coordinates
SUMXY: sum of the xy-crossproducts (x-coord*y-coord)
SUMX2: sum of squares of the x-coordinates
SUMY2: sum of squares of the y-coordinates
where the operations take place for all the pixels that belong to the target object.

If Npxs is the number of pixels that belong to the target object, the following mathematical equations can be used to generate the moments $M[i,j]$ of the target object, for $i=0$ to 2 and $j=0$ to 2:

$$M[0,1]: SUMY/Npxs \qquad (1)$$

$$M[1,0]: SUMX/Npxs \qquad (2)$$

$$M[0,2]: SUMY2-(SUMY)^2/Npxs \qquad (3)$$

$$M[2,0]: SUMX2-(SUMX)^2/Npxs \qquad (4)$$

$$M[1,1]: SUMXY-(SUMX*SUMY)/Npxs \qquad (5)$$

As the contour following algorithm tracks the border, the perimeter of the target object is also calculated by a simple cumulative process. Other morphological properties of the target objects which can be derived from the moments are:

$$\text{slope} = 0.5 * \text{arctangent}(2*M[1,1]/(M[2,0]-M[0,2])) \quad (6)$$

$$\text{elongation} = (Mp[2,0]/Mp[0,2])^{\frac{1}{2}} \quad (7)$$

where $$Mp[2,0] = M[0,2] * (\text{sine}(\text{slope}))^2 +$$
$$M[2,0] * (\text{cosine}(\text{slope}))^2 +$$
$$2*(\text{sine}(\text{slope}))*(\text{cosine}(\text{slope}))$$

and $$Mp[0,2] = M[2,0] * (\text{sine}(\text{slope}))^2 +$$
$$M[0,2] * (\text{cosine}(\text{slope}))^2 +$$
$$2*(\text{sine}(\text{slope}))*(\text{cosine}(\text{slope}))$$

$$\text{area} = \text{Npxs} \quad (8)$$

$$\text{irregularity} = \text{perimeter}/\text{pericircle} \quad (9)$$

where pericircle is the perimeter of a circle with substantially the same area as the target object.

The sizes of the image components can be classified by means of phi diameter distributions in which $\text{phi} = -\log_2 (\text{particle diameter})$.

The morphological properties of the target objects present in the area of interest of the digitized image can be in a file system. The results of the analysis of different images may be combined so that meaningful statistical measures can be obtained from a set of samples. In the preferred embodiment, the results of the statistical analysis are displayed in graphic form as distribution and cumulative functions. Additionally, statistical parameters, customized for the application, are calculated and overimposed on the graphics display. FIGS. 4-7 illustrates some of these results.

Figure 7:
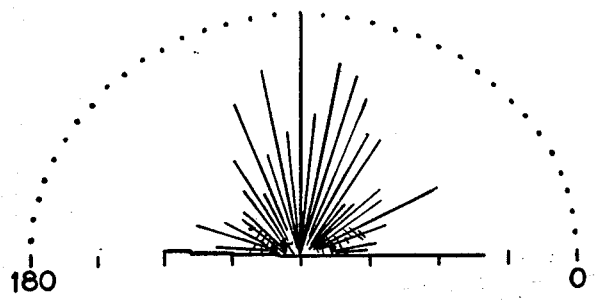

FIG. 7 is of particular interest in that it shows how one can obtain a slope of the components by means of semicircular projections of the orientation of the components.

The graphical output as well as any derived images may be displayed on the monitor 26 and/or a printer not shown. The graphical output of the statistical distributions generated by the system may be directly used in: (1) the morphological characterization of organic matter present in samples; (2) the morphological characterization of mineral samples present in petrographic thin sections; (3) the interpretation of the morphological characterization and quantification of void (pore) space in the sample images by selecting a negative slope line transformation; and (4) the automatic classification of rocks by means of percentual mineral composition with classification based on commonly used petrographic standard classifications.

It is further possible to process the above information as a cummulative areal counter where the total area of similar groups of image components are accumulated and the percentages against the total area of the rest of the group are calculated. Techniques for doing this are explained in the aforementioned paper by Lorente which is hereby incorporated by reference herein.

It is to be understood that the invention is not limited to the illustrations and explanations described and shown herein, which are intended to be illustrative of the best modes of carrying out the invention and which are susceptible to modification of form, size, arrangement of parts, and details of operation. The invention is intended to encompass all such modifications and variations which are within its spirit and scope as defined by the claims.

What is claimed is:

1. A process for image digital analysis to achieve morphological characterization of image components which comprises:
   capturing an original image from at least one of a microscope and a photograph;
   electronically digitizing said image into a digital matrix representing two dimensions;
   transferring said digitized image to a video monitor;
   modifying said digitized image;
   processing two dimensional data obtained from said digitized image into statistical distributions;
   interpreting said digitized image wherein said interpreting step comprises transforming said processed data into said statistical distributions; classifying the sizes of said image components by means of phi diameter distributions; characterizing relative elongation of said image components by means of moments of the statistical distributions associated with each component being sampled; characterizing the irregularity of each said component by comparing measurements of its perimeter to the perimeter of a substantially equiareal circle; and obtaining a slope of said components by means of semicircular projections of the components orientation; and
   generating a graphical output of said statistical distributions.

2. A process according to claim 1 wherein said image capturing step comprises continually viewing images from said microscope or from a plurality of photographs with a video camera.

3. A process according to claim 2 wherein said modifying step includes improving said digitized image by deleting unwanted noise and adding missing components.

4. A process according to claim 3 wherein said modifying step further includes modifying a range of input and output gray-level of said image by means of hardware implemented input and output look-up tables.

5. A process according to claim 3 wherein said modifying step further includes selecting a restricted group of gray levels and filtering the image using said selected group of gray-levels.

6. A process according to claim 1 wherein said processing step comprises deriving further digitized images by performing at least one of a mathematical and logical operation to define borders of said components of said image.

7. A process according to claim 6 wherein said interpreting step includes obtaining morphological parameters including at least one of the area, perimeter, relative elongation, irregularity and slope of each image component using moment generation of a target object.

8. A process according to claim 6 wherein said processing step further includes defining said borders of said image components using eight connectivity criteria and a cumulative pixel based feature operation allowing the recognition of internal and external borders of an image component.

9. A process according to claim 2 which further comprises providing a display monitor and a storage memory, storing each said digitized image in said memory and displaying a desired improved digitized image on said monitor.

10. A process according to claim 1 which further includes processing as a cumulative areal counter where the total area of similar groups of image components are accumulated and the percentage against the total area of the rest of the group are also calculated.

11. A process according to claim 1 which further includes continuous processing of several digitized images and accumulating processed data from said several digitized images.

12. A process according to claim 1 further comprising directly using said generated graphical output of said statistical distributions in the morphological characterization of sample images.

13. A process according to claim 1 further comprising directly using said generated graphical output of said statistical distributions in the morphological characterization of samples present in organic matter.

14. A process according to claim 1 further comprising directly using said generated graphical output of said statistical distributions in the morphological characterization of mineral samples present in petrographic thin sections.

15. A process according to claim 1 further comprises directly using said generated graphical output of said statistical distributions in interpretation of the morphological characterization and quantification of void (pore) space in the sample images.

16. A process according to claim 10 further including classifying rocks automatically by means of percentual mineral composition.

* * * * *